United States Patent [19]
Belgorod

[11] Patent Number: 6,086,888
[45] Date of Patent: Jul. 11, 2000

[54] ANALGESIC COMPOSITIONS FROM SWEET BELL PEPPERS AND METHODS OF USE THEREOF

[75] Inventor: Barry Miles Belgorod, New York, N.Y.

[73] Assignee: BMB Patent Holding Corporation, New York, N.Y.

[21] Appl. No.: 09/218,680

[22] Filed: Dec. 22, 1998

[51] Int. Cl.$^7$ ................................................. A01N 65/00
[52] U.S. Cl. ...................................................... 424/195.1
[58] Field of Search ........................................ 424/195.1

[56] References Cited

U.S. PATENT DOCUMENTS

| | | |
|---|---|---|
| 4,313,958 | 2/1982 | LaHann . |
| 4,400,398 | 8/1983 | Coenen et al. ........................... 426/429 |
| 4,564,633 | 1/1986 | LaHann et al. . |
| 4,783,465 | 11/1988 | Sunshine et al. ........................ 514/255 |
| 4,980,190 | 12/1990 | Dunham . |
| 5,021,450 | 6/1991 | Blumberg . |
| 5,232,684 | 8/1993 | Blumberg et al. . |
| 5,536,506 | 7/1996 | Majeed et al. ........................... 424/464 |
| 5,660,830 | 8/1997 | Anderson .............................. 424/195.1 |
| 5,665,360 | 9/1997 | Mann .................................... 424/195.1 |
| 5,674,496 | 10/1997 | Eiscorn et al. ........................ 424/195.1 |
| 5,744,161 | 4/1998 | Majeed et al. ........................... 424/464 |
| 5,891,465 | 4/1999 | Keller et al. ............................ 424/450 |
| 5,910,512 | 6/1999 | Conant .................................... 514/617 |

OTHER PUBLICATIONS

Computer Abstract Derwent 1987:110845 HU41000T Mar. 30, 1987 "Separation and Purification of Capsaicin . . . ".
Rowland et al. (1983) "Capsaicin Production in Sweet Bell and Pungent Jalapeno Peppers", J. Agric. Food Chem 31:484–487.
Yuan et al. (1996) "Biostrategies in the Pacific Rim", Genetic Engineering News p. 29 & p. 32.
Geoffery A. Cordell et al. (1993) "Capsaicin: Identification, Nomenclature, and Pharmacotherapy", The Annals of Pharmacotherpy 27:330–336.
Govindarajan (1986) "Capsicum–Production, Technology, Chemistry, and Quality, Part I", CRC Critical Reviews in Food Science and Nutrition 22–2:109–176.
Govindarajan (1986) "Capsicum–Production, Technology, Chemistry, and Quality, Part II", CRC Critical Reviews in Food Science and Nutrition 23–3:207–283.
Govindarajan (1986) "Capsicum–Production, Technology, Chemistry, and Quality, Part III", CRC Critical Reviews in Food Science and Nutrition 24–3:245–355.
Govindarajan (1987) "Capsicum–Production, Technology, Chemistry, and Quality, Part IV", CRC Critical Reviews in Food Science and Nutrition 25–3:185–282.
Govindarajan (1991) "Capsicum–Production, Technology, Chemistry, and Quality, Part V", CRC Critical Reviews in Food Science and Nutrition 29–6:435–474.
Rouhi (1996) "Chili Pepper Studies Paying Off With Hot Birdseed and Better Analgesics", C & EN pp. 30–31.
Fuller (1990) "The Human Pharmacology of Capsaicin", Arch. Int. Pharmacadyn. 303: 157–199.
Levenson (1995) "Accounting for Taste", The Science Jan., Feb.:15–16.
"Merriam–Webster's Collegiate Dictionary, Tenth Edition", Merriam–Webster, Inc., Springfield, MA, pp. 860 and 861 (1996).
"The Merck Index: An Encyclopedia of Chemicals, Drugs, and Biologicals, Tenth Edition", Merck & Co., Inc., Rahway, NJ, pp. 1741 and 1742, Entry #1741, 1983.
Anon (1994) Sweet Success, Chemistry & Industry, 18:705.
Matsushita (1968) "Changes of Free Sugar Contents in Sarcocarp and Seed During the Ripening Process. Free Sugar Contents in Pumpkin, Sweet Pepper, and Trifoliate Orange", Eiyo To Shokuryo, 21(3), 185–8.
Somos (1971) "Catalase Activity and Glucose, And Ascorbic Acid Content Of Some Sweet Pepper Sorts", Kerteszetiegyetem Kozlem., 34(2), 5–16.
Butkevich (19659) "Buildup of Carbohydrates in Sweet Peppers During Ripening", Tr. Mold. Nauch.–Issled. Inst. Oroshaemogo Zemled. Ovoshchevod., 10(1), 63–8, 1969.

*Primary Examiner*—Herbert J. Lilling

[57] ABSTRACT

This invention relates to analgesic compositions obtained from extracts of sweet bell pepper purees or filtrates thereof and to therapeutic uses of such analgesic compositions.

33 Claims, 6 Drawing Sheets

ANALGESIC COMPOSITIONS FROM SWEET BELL PEPPERS AND METHODS OF USE THEREOF

FIELD OF THE INVENTION

This invention relates to analgesic compositions obtained from sweet bell peppers and to therapeutic uses of such analgesic compositions.

BACKGROUND

A primary focus of drug research is the development of analgesics to be used in pain management. New analgesics are often derived from herbs or plants. For example, capsaicin, a vanillyl alkaloid which is the pungent component of hot peppers, is an analgesic. (Cordell and Araujo (1993) *The Annals of Pharmacotherapy* 27:330; Levinson (1995) *The Sciences* January/February: 13–15)). Therapeutically capsaicin has been used successfully to treat several painful conditions including rheumatoid arthritis, osteoarthritis, and various peripheral neuropathic disorders. (Cordell and Araujo (1993)). However, the usefulness of capsaicin as a therapeutic is limited by its adverse effects including burning and erythema. Moreover, these side effects can persist over time.

Given the comprehensive therapeutic applications of analgesics, there is an enormous medical and health requirement for analgesics with limited side effects.

SUMMARY OF THE INVENTION

It is an object of this invention to provide analgesic compositions obtained from sweet bell peppers.

In particular, it is an object of this invention to provide analgesic compositions comprising an analgesically active fraction of an extract of sweet bell pepper puree or filtrate thereof.

It is yet another object of this invention to provide methods of producing the analgesic compositions described herein as well as methods of use of those analgesic composition.

DESCRIPTION OF FIGURES

FIG. 3 shows an HPLC trace of an acetone extract of fraction 5. The samples for FIGS. 1–3 were subjected to HPLC analysis using an ODL3 reverse-phase HPLC column (15 cm×4.6 mm ID stainless steel column) and eluted with a 65/35 mixture of methanol/1% aqueous acetic acid at 1 ml/min.

DETAILED DESCRIPTION OF THE INVENTION

This invention relates to analgesic compositions obtained from sweet bell peppers and to therapeutic uses thereof. The experiments described in the Examples demonstrate that the analgesic component of the analgesic compositions of the invention is not capsaicin or dihydrocapsaicin.

The analgesic compositions described herein may be produced in a variety of ways. In one embodiment the compositions of the invention are prepared by:

(a) fractionating an extract of a puree of sweet bell peppers or a filtrate thereof by chromatography with a suitable solvent or solvent mixture; and (b) identifying a fraction produced by step (a) which has analgesic activity.

The puree to be extracted in step (a) may be made by pureeing sweet bell peppers by hand or by mechanical means. The stems and seeds of the peppers may be removed prior to preparation of the puree. By way of example, green, yellow or red sweet bell peppers may be used to make the puree. The puree may be extracted directly or it may first be concentrated or diluted with an appropriate diluent, such as water, prior to extraction. Preferably, the puree is subjected to a filtration step, such as vacuum filtration, prior to extraction. The resultant filtrate is then extracted as described below.

The puree or filtrate thereof may be extracted by conventional methodology. In one embodiment, an alcohol extraction may be performed by conventional methodology. By way of example, the sweet pepper puree or filtrate thereof may be extracted with short chain alcohols. Examples of short chain alcohols include, but are not limited to, methanol, ethanol and 2-propanol. In a preferred embodiment, methanol is used to extract the bell pepper puree or filtrate thereof.

Once the puree or filtrate has been extracted, the extract is then fractionated by chromotography. Examples of the types of chromotography which may be utilized to fractionate the extracts of the invention include, but are not limited to, high pressure liquid chromatography, gas chromotography, column chromotography and thin layer chromotography.

Solvents or solvent mixtures suitable for use with the types of chromotography recited above are solvents or solvent mixture which are capable of separating molecules based on their polarity. Examples of such solvent or solvents mixtures include, but are not limited to, short chain alcohols and mixtures of short chain alcohols and water.

For example, as described in Examples 3 and 4, a fraction (fraction 5) eluted from a polyamide column with a solvent mixture of 80% methanol: 20% water (vol:vol) possessed analgesic activity as measured by a rat-tail flick assay.

Fractions produced by chromatographic separation may therefore be tested for analgesic activity using assays such as the rat tail flick assay described in the Examples. Based on the data presented in the Examples, it is expected that chromatographic fractions eluted with a moderately polar solvent system will possess analgesic activity.

The analgesic compositions of the invention therefore comprise the analgesically active fraction of extracts of sweet bell pepper purees or filtrates thereof.

It is preferred that upon chromatographic separation, the fraction possessing analgesic activity is concentrated to dryness and then resuspended in an aqueous solution suitable for administration to animals or humans, such as water or phosphate-buffered saline.

The formulations of the present invention therefore comprise an analgesically active fraction of an extract of sweet pepper puree or a filtrate thereof, where the fraction is optionally admixed together with one or more pharmaceutically acceptable carriers and, and also optionally with other therapeutic ingredients. The carrier(s) must be compatible with other ingredients of the formulation and not deleterious to the recipient thereof. The formulations may be conveniently prepared in unit dosage form and may be prepared by any method well-known in the pharmaceutical art.

All methods include the step of bringing into association the analgesically active fraction with the carrier which constitutes one or more accessory ingredients. In general, the formulations are prepared by uniformly and intimately bringing into association the analgesically active fraction with liquid carriers or finely divided solid carriers or both, and then, if necessary, shaping the product into the desired formulation.

Formulations suitable for intravenous, intramuscular, subcutaneous, intraarticular, intrathecal or intraperitoneal administration conveniently comprise sterile aqueous solutions of the fraction having analgesic activity with solutions which are preferably isotonic. Such formulations may be conveniently prepared by dissolving a concentrate of the analgesically active fraction in water containing physiologically compatible substances such as isotonic sodium chloride, glycine, and the like, and having a buffered pH compatible with physiological conditions to produce an aqueous solution, and rendering the solution sterile. These may be present in unit or multi-dose containers, for example, sealed ampoules or vials.

The formulations of the present invention may incorporate a stabilizer. Illustrative stabilizers are polyethylene glycol, proteins, saccharides, amino acids, inorganic acids, and organic acids which may be used either independently or as admixtures. Two or more stabilizers may be used. These stabilizers may be used in aqueous solutions at the appropriate concentration and pH.

Additional pharmaceutical methods may be employed to control the duration of action. Controlled release preparations may be achieved by using polymers to complex or absorb the present active ingredient. The controlled delivery may be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the present active material into particles of a polymeric material such as polyesters, polyamino acids, hydrogels, poly(lactic acid) or ethylene vinylacetate copolymers. Alternatively, instead of incorporating these materials into polymeric particles, it is possible to entrap these materials in microcapsules prepared, for example, by coacervation techniques or by interfacial polymerization, for example, hydroxymethylcellulose or gelatin-microcapsules and polymethylmethacrylate microcapsules, respectively, or in colloidal drug delivery systems, for example, liposomes, albumin microspheres, microemulsions, nanoparticles, and nanocapsules or in macroemulsions.

When oral preparations are desired, the compositions may be combined with typical carriers, such as lactose, sucrose, starch, talc magnesium stearate, crystalline cellulose, methyl cellulose, carboxymethyl cellulose, glycerin, sodium alginate or gum arabic among others.

Other modes of administration include, but are not limited to, topical: such as, ophthalamic, oral, nasal, vaginal, rectal, dermatological, and via inhalation. The preparation of formulations suitable for such modes of administration is well known to those in the art. Therefore, the skilled artisan would be able to select the proper formulation ingredients.

The analgesic compositions of this invention may be pharmacologically and therapeutically useful where analgesics have been used in the prior art, including, but not limited to, the management of acute pain, chronic pain, neuralgias, other neurogenic pain syndromes, and post-operative pain in a subject. The therapeutically useful dosage of the analgesic used in the given therapy or treatment will vary depending on the seriousness of the condition, the time the individual has been afflicted with the condition, the weight of the individual, efficacy of the present active material and other parameters known to one skilled in the art. Based on such parameters, the treating artisan will determine the therapeutically effective amount of the composition to be used for a given individual. Such therapies may be administered as often as necessary and for the period of time judged necessary by the artisan administering the treatment.

The present invention also provides a method of treating subjects afflicted with a condition amenable to analgesic treatment which comprises the step of administering to the subject a therapeutically effective amount of the analgesic composition of the invention, optionally with a pharmaceutically acceptable composition as described above. Administration of the analgesic composition may be for either a prophylactic or therapeutic use. When provided prophylactically, the composition is provided in advance of any symptom which might arise in the absence of analgesic treatment. When provided therapeutically, the composition is provided at (or shortly after) the onset of any symptoms. The therapeutic administration of the present composition serves to attenuate the painful condition. Examples of conditions that can be treated by this method include, but are not limited to, post operative, conjunctival, nasal, otic, rectal and vaginal pain.

The therapeutically effective amount of the analgesic composition to be used in the aforementioned treatments will vary depending on the seriousness of the pain. One of skill in the art will know the parameters to evaluate the response of the subject to the present compositions and establish the dosage based on those parameters.

All books articles or patents referenced herein are incorporated by reference. The following examples illustrate various aspects of the invention but are in no way intended to limit the scope thereof.

EXAMPLE 1

Analgesic Effect of Pepper Puree Materials

"Sweet" green bell peppers (*Capsicum annum grossum*) were obtained form the grocery section of a local supermarket. The stems and seeds were removed and discarded, and the skin was cut into small, 1/2 in., squares. The pieces, 476 g, were pureed in a blender to a green mush. The puree was vacuum filtered (slowly) to give 260 mL of green aqueous suspension. The green suspension was again suction filtered giving 260 mL of green suspension filtrate topped with some foam.

The filtrate was apportioned as follows:

Preparation Designation & Description

A: 70 milliliter (mL) of filtrate

B. 35 mL of filtrate plus 35 mL of water

C. 7 mL of filtrate plus 63 mL of water

The filtered residue, solid green puree, was mixed with 200 mL of water, stirred and refiltered, to give 155 mL of pale green suspension. This suspension was apportioned as follows Preparation Designation & Description D: 70 mL of resuspension E: 35 mL of resuspension plus 35 mL of water Rat Tail Flick Trails The rat tail flick list is a classic animal model designed to detect and evaluate agents which elevate the threshold for perception of pain. In this model, a pharmacologically altered pain threshold would result in a delay of rat tail flick to avoid a noxious stimulus, such as a heat lamp.

In this Example, the rats' tails were dipped briefly (1–3 sec) in the liquid; were allowed to air dry, then subjected to a heat lamp. Time was measured to the first tail flick response.

Preparation Designation and Description

A: baseline 2.54 sec. Trial (avg) 8.60 sec

C: baseline 2.37 sec. Trial (avg) 6.52 sec

D: baseline 2.83 sec. Trial (avg) 5.43 sec

EXAMPLE 2

Materials

Sweet Red Peppers

Sweet red peppers were obtained, cut and pureed as before. 258 g of red peppers gave 157 mL of a red-orange opaque filtrate.

Preparation Designation & Description

F: 70 mL of red pepper filtrate

Yellow Bell Peppers

Sweet yellow bell peppers were obtained, cut and pureed as above. 246 g of peppers gave 150 mL of yellow opaque filtrate.

Alcohol Extracts of Green Bell Peppers

Stems and seeds were removed from 4 green peppers as before, and 436 g of small pieces of pepper were pureed. Suction filtration of the puree gave 275 mL of green suspension. This mixture was concentrated under reduced pressure (water pump, rotary evaporator) at 50° C. for 3 hr. A mixture of green solid and solution resulted: weight 12.5 g. The mixture of solid and solution was mixed with 100 mL of methanol, stoppered, and kept at room temperature for 65 hr, then gravity filtered, resulting in a clear green solution. This solution was concentrated under reduced pressure, affording 8.00 g of green foam.

The residue from concentration of the methanol extract was covered with 70 mL of water. Swirling the mixture for 10 minutes (min.) produced an opaque green solution. All of the extract residue dissolved.

Preparation Designation & Description

H: 70 mL of MeOH residue dissolved in water.

I: 10% dilution of H in water

J: 1% dilution of H in water

K: 0.1% dilution of H in water

TABLE I

| Preparation Description | n* | Tail-Flick Test 0 minutes** | 30 minutes*** |
|---|---|---|---|
| Baseline+ (NO WATER IMMERSION) | 20.0 | 2.76 (0.11) | |
| Water Immersion | 5 | 4.76 (0.39) | 2.64 (0.09) |
| A: Green Pepper Filtrate (100%) | 6 | 7.21 (0.81) | 2.78 (0.25) |
| B: Green Pepper Filtrate (50%) | 6 | 6.44 (0.60) | 3.12 (0.34) |
| C: Green Pepper Filtrate (100%) | 6 | 6.10 (0.41) | 3.07 (0.33) |
| D: Green Pepper residue extract (100%) with $H_2O$ | 6 | 5.98 (0.38) | 2.97 (0.38) |
| E: Green Pepper residue extract (50%) with $H_2O$ | 6 | 5.69 (0.38) | 3.12 (0.40 |
| F: Red Pepper Filtrate (100%) | 6 | 5.64 (0.45) | 3.05 (0.34) |
| G: Yellow Pepper Filtrate (100%) | 6 | 4.91 (0.19) | 2.77 (0.20) |
| H: Green Pepper Methanol (100%) | 6 | 8.49 (0.45) | 3.87 (0.24) |
| I: Green Pepper Methanol (100%) | 6 | 7.13 (0.46) | 3.05 (0.35) |
| J: Green Pepper Methanol (1%) | 8 | 6.03 (0.42) | 3.25 (0.34) |
| K: Green Pepper Methanol (0.1%) | | 5:30 (0.13) | 3.06 (0.18) |

+Baseline, animals received no treatment
n* = number of animals
** $1^{st}$ test after drying of applied preparation
***reapplication of noxious stimuli
The numbers in parenthesis represent the standard error of the mean As shown in Table I, there is an enhanced analgesic effect with green and red peppers. The greatest analgesic effect was found in the filtrate of the green pepper puree at 100% concentration, and the resuspended aqueous solution of the methanol extract of the green pepper puree at 100% and 10% concentrations. The resuspended aqueous solution of the methanol extract of the green pepper puree at 100% concentration exhibited the most prolonged duration of action.

EXAMPLE 3

Stems and seeds were removed from 4.349 kg of green bell peppers, obtained from a local supermarket. The green rinds were cut into small pieces, then pureed in a Waring Blender. The resulting mush was filtered by suction, and the filtrate was evaporated under reduced pressure at $\leq 45°$ C., leaving 202.1 g of green gum. This was covered with 1.0 L of methanol, and the mixture was stirred at room temperature for 10 days. The methanol extract was filtered by suction, then concentrated under reduced pressure at $\leq 45°$ C., giving 69.4 g of green gummy residue. This residue was dissolved in 176 mL of water, giving a dark green solution (total volume=226 mL).

The aqueous solution of the methanolic extract was fractionated on a polyamide resin as follows:

200 g of polyamide resin (Alltech Assoc., Cat. #09062) was mixed with 60 mL of water and added to a 5 cm diameter glass column. Slight air pressure was applied, resulting in a 60 cm water packed column of polyamide. To this column was added 43 mL of the aqueous solution of methanolic extract residue prepared above. The column was then eluted in sequence with 1.0 L volumes of 1) water, 2) 20% methanol/80% water (vol:vol); 3) 40% methanol/60% water, 4) 60% methanol/40% water) 80% methanol/20% water; and 6) pure methanol and each eluate was concentrated to dryness under reduced pressure and then dissolved in 70mL of water.

These solutions were used to test for rat tail-flick response time by dipping rats' tails for 10 second in an aqueous solution of the test material, briefly drying with a tissue and then subjecting the tails to an intense light beam. Time (in seconds) was measured to the first tail-flick response. Baseline values were obtained for each rat prior to contact with the test solution, and a value for pure water as a test material was also obtained. The eluate from fractions 1–4 and 6 possessed little, if any, analgesic activity. The eluate from the 80% methanol wash, designated fraction 5, possessed analgesic activity when tested in six (#1–#6) rats as shown below in Table II.

TABLE II

Rat Tail-Flick Response

| Rat | Flick-Time(s) | 30 min later |
|---|---|---|
| #1 | 10.3 | 6.8 |
| #2 | 8.5 | 4.6 |
| #3 | 2.2 | 4.4 |
| #4 | 7.2 | 3.9 |
| #5 | 5.8 | 4.2 |
| #6 | 12.0 | 5.8 |
| Avg | 7.7 | 4.9 |
| Water | 4.8 | 2.6 (average of 5 rats) |

HPLC Analysis of Fraction 5

Figure 1:
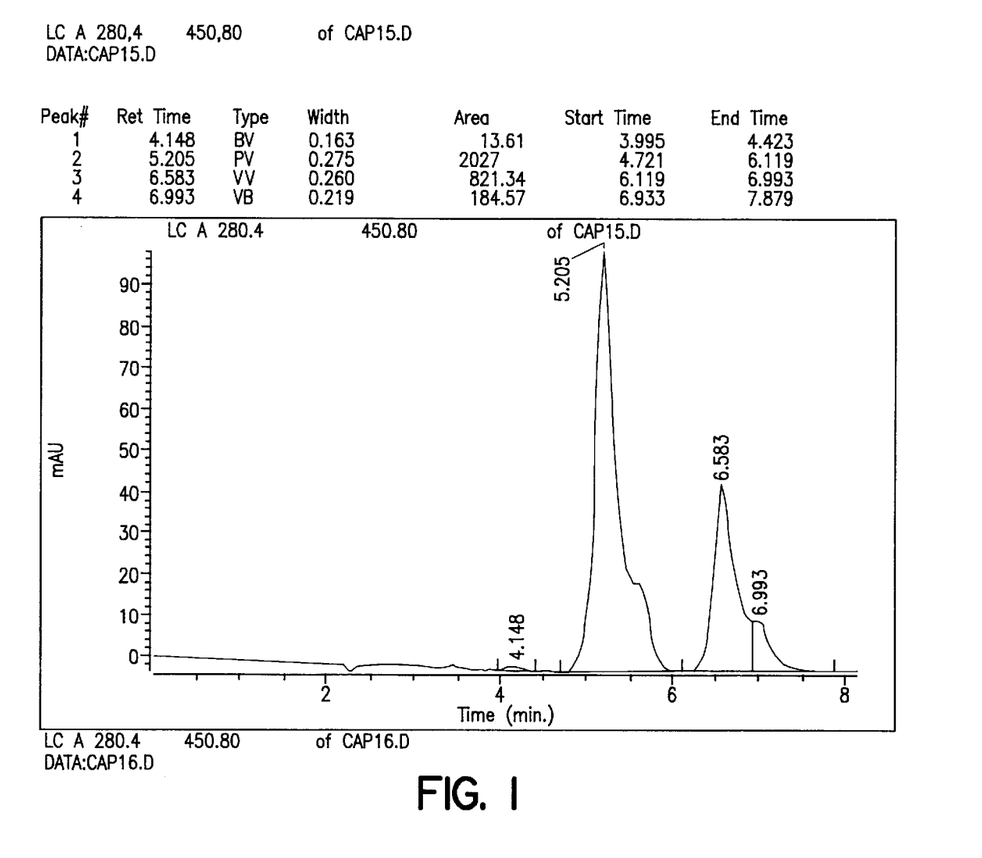
FIG. 1 shows an HPLC trace of a roughly 2:1 mixture (ppm:ppm) of pure capsaicin: dihydrocapsaicin.

Capsaicin available as (Aldrich Chem. Co. Cat. #36,037-6) a roughly 2:1 mixture (ppm:ppm) of capsaicin and dihydrocapsaicin was injected onto a Partisil 5 micron ODS3 reverse-phase HPLC column (15 cm×4.6 mm ID stainless steel column), and eluted with a 65/35 mixture of methanol/1% aqueous acetic acid at 1 ml/min. Two peaks were observed at 5.2 minutes (capsaicin) and 6.6 minutes (dihydrocapsaicin) (FIG. 1). These compounds could be detected to a level ≧20 ppm.

Figure 2:
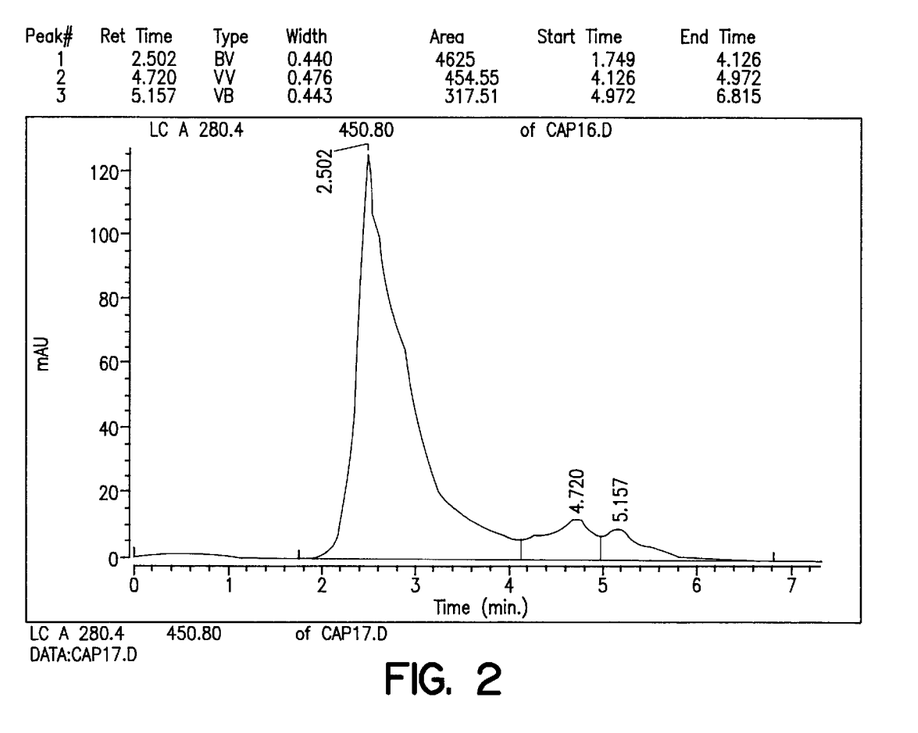
FIG. 2 shows an HPLC trace of the fraction (fraction 5) eluted from a polyamide column with an 80:20 (vol:vol) methanol/water mixture.

By comparison, injection of the tail-flick test solution from fraction 5 onto the same column followed by elution with a 65/35 mixture of methanol/1% acetic acid at 1 ml/min produced two small peaks at 4.7 and 5.1 minutes (FIG. 2).

However, as capsaicin and dihydrocapsaicin have a UV maximum at 280 μm, while the peaks at 4.7 and 5.1 min in fraction 5 had a minimum at that wavelength and a maximum at 320 μm (data not shown), the two peaks at 4.7 and 5.1 minutes in FIG. 2 were neither capsaicin (5.2 min) nor dihydrocapsaicin (6.6 min) by virtue of both their HPLC retention times and UV absorption spectra.

Moreover, capsaicin was not detected in HPLC traces of an acetone extract of fraction 5 (FIG. 3) or in HPLC traces of fraction 5 concentrated to dryness (data not shown) and dissolved in 7 mL of water (10×the concentration of fraction 5 analyzed in FIG. 2).

Figure 3:
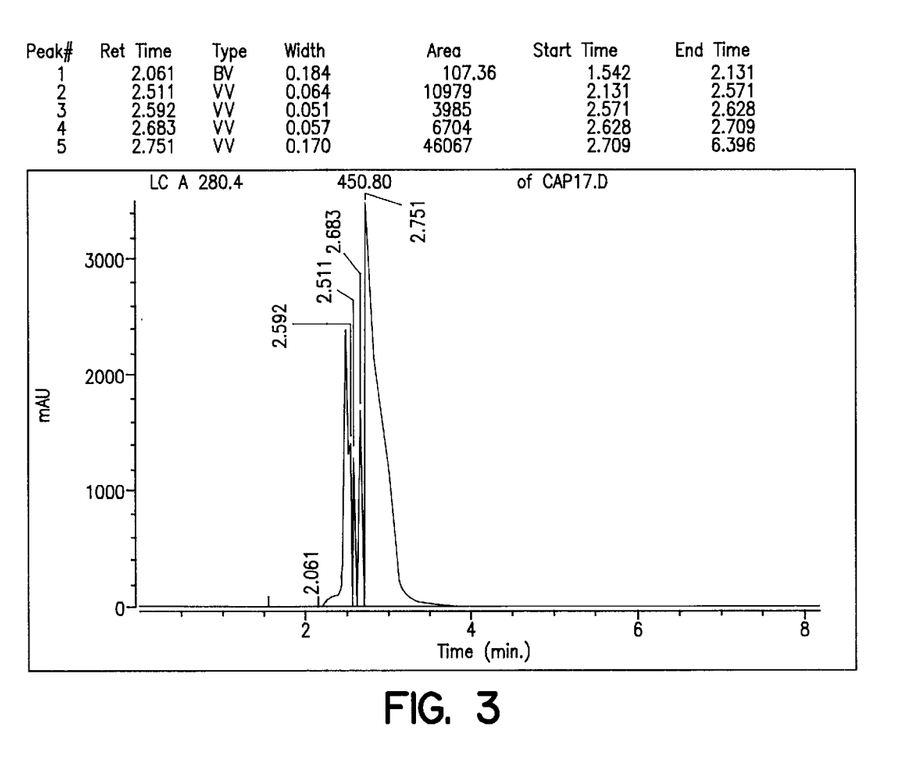

The data shown in FIGS. 1–3 therefore demonstrate that neither capsaicin nor dihydrocapsaicin are responsible for the analgesic effect observed with fraction 5.

EXAMPLE 4

To confirm that capsaicin's elution time off the HPLC column was not shifted because of its presence in the sweet pepper extract as a complex with another molecule, 10 mg of capsaicin (equivalent to 133 ppm) was added to the sweet bell pepper filtrate prepared as described in Example 3 and the filtrate was then fractionated on a polyamide column as described in Example 3.

The 4th, 5th, and 6th (60, 80 and 100% MeOH) fractions were concentrated to dryness, and the residues were each dissolved in 75 mL of water to form the aqueous solutions. Fraction 5 had previously shown analgesic activity in the rat tail-flick test (see Table II). These solutions, as well as pure capsaicin and dihydrocapsaicin (Aldrich), were then subjected to HPLC analysis using a Beckman ultrasphere 5 micron ODS column (15 cm×4.6 mm ID stainless steel column) and were eluted with a 65/35 mixture of methanol/1% aqueous acetic acid at 1 ml/min.

HPLC of fraction 5 (FIG. 4) showed a small peak at ca. 7.5 minutes; HPLC of pure capsaicin and dihydrocapsaicin (FIG. 5) shows peaks at ca. 7.7 and 10.8 minutes; and HPLC of fraction 5 comixed with capsaicin and dihydrocapsaicin in an amount equal to 30 ppm (FIG. 6) showed a peak at ca. 7.6 min.

Figure 4:
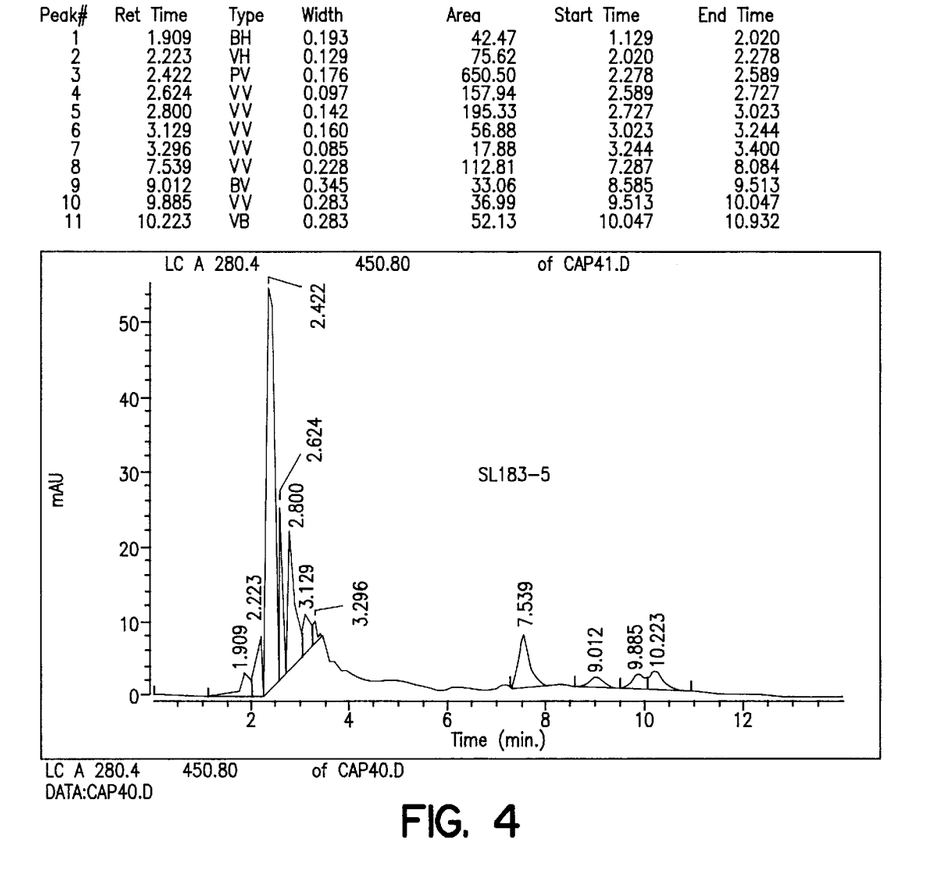
FIG. 4 shows an HPLC trace of fraction 5 prepared from a filtrate of a green sweet bell pepper puree to which 10 mg of capsaicin was added.

However, the peak in fraction 5 with retention time at ca. 7.5 minutes in FIG. 4 was shown to have a UV absorption spectrum different from that of capsaicin (data not shown). Furthermore, from the relative areas of the peaks in FIGS. 4 and 6, it can be concluded that even if the peak at ca. 7.5 in FIG. 4 were capsaicin, no more than ca. 13 ppm of capsaicin, or ca. 10% of the 10 mg amount added to the original puree, could be present in fraction 5. Since Table 7 of Govindarajan (*CRC Critical Reviews in Food Science and Nutrition* (1991) vol 29 (pp 435–474)) shows that capsaicin has a moderate desensitization potential of $7.2\times10^3$ ml/g (which is equivalent to 139 ppm of capsaicin), even assuming arguendo that the peak at ca. 7.5 in FIG. 4 is capsaicin (which UV absorption spectrum shows it was not), the 13 ppm of capsaicin represented by the peak at 7.5 in FIG. 4 could not produce the analgesic effect exhibited by fraction 5 in the rat tail-flick test because it is less than one-tenth the amount of capsaicin (139 ppm) required to produce moderate desensitization.

Figure 5:
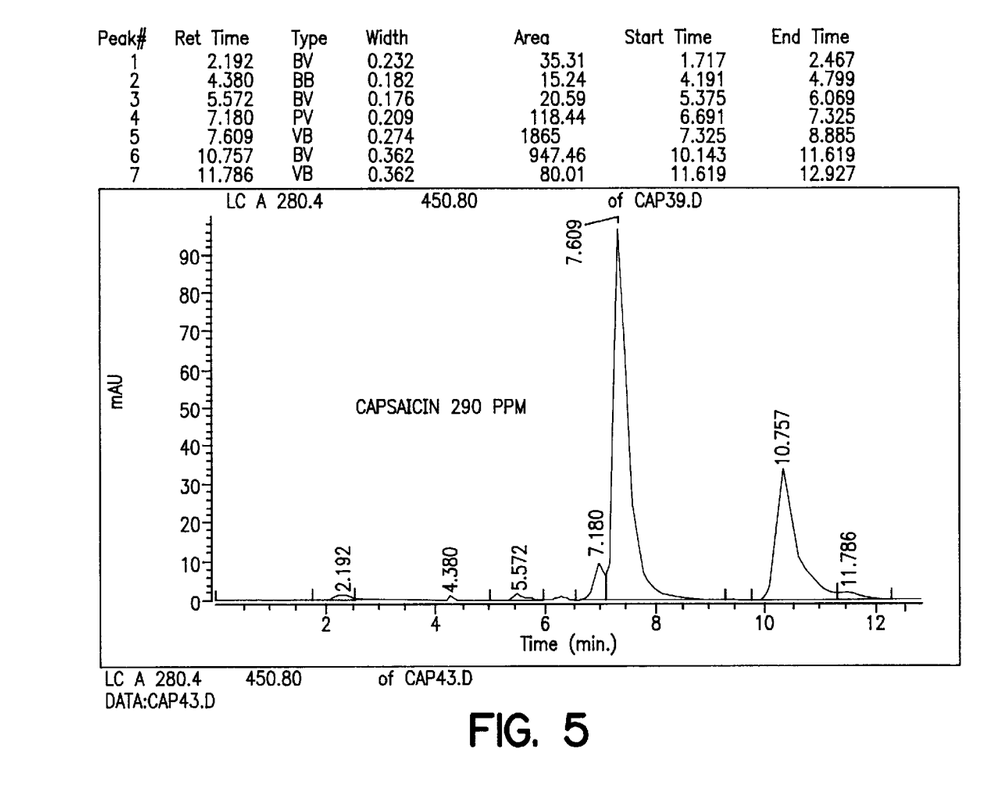
FIG. 5 shows an HPLC trace of pure capsaicin: dihydrocapsaicin in a 2:1 mixture (ppm:ppm).
Figure 6:
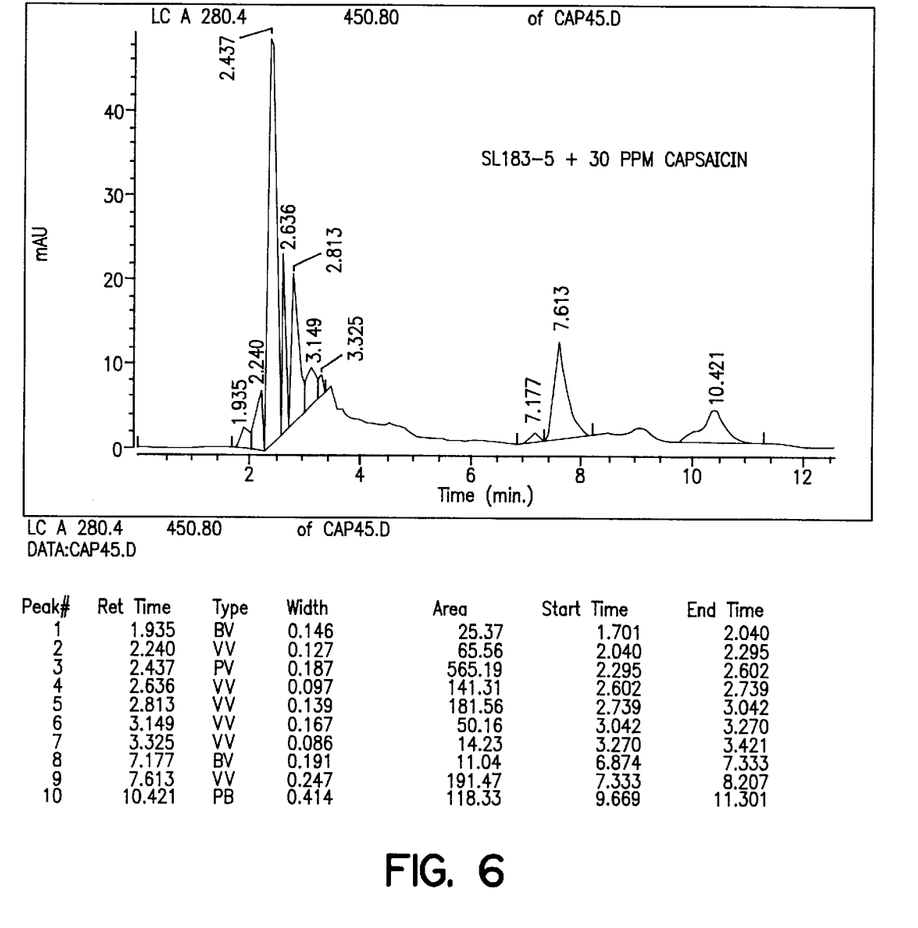
FIG. 6 shows an HPLC trace of fraction 5 comixed with capsaicin and dihydrocapsaicin in an amount equal to 30 ppm. The samples for FIGS. 4–6 were subjected to HPLC analysis using a Beckman ultrasphere 5 micron ODS column (15 cm×4.6 mm ID stainless steel column) and were eluted with a 65/35 mixture of methanol/1% aqueous acetic acid at 1 ml/min.

The data presented in FIGS. 4–6 and in Govindarajan (1991) therefore provide further evidence that neither capsaicin nor dihydrocapsaicin are responsible for the analgesic activity exhibited by the analgesically active fraction of extracts of sweet bell pepper purees or filtrates thereof.

What is claimed is:

1. A composition comprising an effective amount of an analgesically active fraction separated from an alcohol or acetone extract of a sweet bell pepper puree or filtrate thereof, where neither capsaicin nor dihydrocapsaicin are responsible for the analgesic activity of said fraction.

2. The composition of claim 1, wherein the fraction is optionally admixed with a pharmaceutical carrier.

3. The composition of claim 1, wherein the sweet bell pepper is a green, yellow or red bell pepper.

4. The composition of claim 1, wherein the extract is an alcohol extract.

5. The composition of claim 4, wherein the alcohol extract is a short chain alcohol extract.

6. The composition of claim 5, wherein the alcohol extract is a methanol extract.

7. The composition of claim 1, wherein the composition is formulated as a controlled-release formulation.

8. An analgesic composition obtained by: separating an analgesically active fraction from an alcohol or acetone extract of a sweet bell pepper puree or filtrate thereof by chromatography of the extract with a suitable solvent or solvent mixture, where neither capsaicin nor dihydrocapsaicin are responsible for the analgesic activity of said fraction.

9. The composition according to claim 8 wherein the sweet bell pepper is a red, yellow or green bell pepper.

10. The composition according to claim 9 wherein the sweet bell pepper is a green bell pepper.

11. The composition according to claim 8, wherein the extract is an alcohol extract.

12. The composition according to claim 11, wherein the extract is an alcohol extract of a filtrate of a sweet bell pepper puree.

13. The composition according to claim 12, wherein the extract is a short chain alcohol extract.

14. A method for providing analgesia to a subject, said method comprising administering to the subject an effective amount of the composition of claim 1.

15. The method according to claim 14 in which the composition is administered topically, systemically, intramuscularly, subcutaneously, intraperitoneally, intrapleurally, intraarticularly, intrathecally, rectally, vaginally, or by inhalation.

16. The method of claim 14, wherein the composition is optionally admixed with a pharmaceutical carrier.

17. A method for providing analgesia to a subject, said method comprising administering to the subject an effective amount of the composition of claim 8.

18. The method according to claim 17 in which the composition is administered topically, systemically, intramuscularly, subcutaneously, intraperitoneally, intrapleurally, intraarticularly, intrathecally, rectally, vaginally, or by inhalation.

19. The method of claim 17, wherein the composition is optionally admixed with a pharmaceutical carrier.

20. A method of producing an analgesic composition, said method comprising: separating an analgesically active fraction from an alcohol or acetone extract of a sweet bell pepper puree or filtrate thereof by chromatography of the extract with a suitable solvent or solvent mixture, where neither capsaicin nor dihydrocapsaicin are responsible for the analgesic activity of said fraction.

21. The method of claim 20, wherein said extract is an alcohol extract.

22. The method of claim 21 wherein said alcohol extract is short chain alcohol extract.

23. The method of claim 22, wherein said alcohol extract is a methanol extract.

24. The method of claim 20, wherein the sweet bell pepper is a red, yellow or green bell pepper.

25. The method of claim 20, wherein the sweet bell pepper is a green bell pepper.

26. The method of claim 20, wherein the fractionating is performed by chromatography on a polyamide column.

27. The method of claim 26, wherein the fractionating uses an alcohol-water solvent mixture.

28. The method of claim 27, wherein the alcohol in the solvent mixture is a short-chain alcohol.

29. The method of claim 28, wherein the short chain alcohol is methanol.

30. The method of claim 29, wherein the solvent mixture is a mixture (vol:vol) of 80% methanol: 20% water.

31. The composition of claim 1, wherein the extract is an acetone extract.

32. The composition of claim 8, wherein the extract is an acetone extract.

33. The method of claim 20, wherein the extract is an acetone extract.

* * * * *